United States Patent [19]

Zoeller

[11] Patent Number: 4,578,368

[45] Date of Patent: Mar. 25, 1986

[54] CATALYST RECOVERY PROCESS

[75] Inventor: Joseph R. Zoeller, Kingsport, Tenn.

[73] Assignee: Eastman Kodak Company, Rochester, N.Y.

[21] Appl. No.: 730,604

[22] Filed: May 6, 1985

[51] Int. Cl.[4] .............................................. B01J 38/62
[52] U.S. Cl. ..................................... 502/28; 260/549; 423/22; 562/607
[58] Field of Search .................... 502/28, 29; 260/549; 562/607; 423/22

[56] References Cited

U.S. PATENT DOCUMENTS

| | | | |
|---|---|---|---|
| 4,252,741 | 2/1981 | Porcelli et al. | 260/549 |
| 4,255,591 | 3/1981 | Makin et al. | 260/549 |
| 4,340,570 | 7/1982 | Davidson | 260/549 |
| 4,358,411 | 11/1982 | Porcelli et al. | 260/549 |
| 4,364,907 | 12/1982 | Barnes | 260/549 |
| 4,388,217 | 6/1983 | Hembre et al. | 502/28 |
| 4,434,240 | 2/1984 | Pugach | 502/29 |
| 4,434,241 | 2/1984 | Larkins, Jr. | 502/28 |
| 4,476,237 | 10/1984 | Porcelli | 502/28 |
| 4,476,238 | 10/1984 | Palmer et al. | 502/28 |
| 4,500,474 | 2/1985 | Gauthier-Lafaye | 260/549 |

Primary Examiner—John Doll
Assistant Examiner—Anthony McFarland
Attorney, Agent, or Firm—Clyde L. Tootle; J. Frederick Thomsen

[57] ABSTRACT

Disclosed is a process for the recovery of noble metals from a catalyst-tar formed in a process in which acetic anhydride is prepared by carbonylating methyl acetate in the presence of a noble metal containing catalyst such as rhodium, lithium and methyl iodide. The rhodium is recovered from the tar formed in the process by treating the catalyst containing tar with a lower fatty acid at a temperature of at least 100° C. thereby isolating the noble metal which precipitates from the tar.

4 Claims, No Drawings

CATALYST RECOVERY PROCESS

DESCRIPTION

This invention relates to a novel process for recovering noble metals and, more particularly, to a method for recovering noble metals such as rhodium from "tars" formed during the preparation of acetic anhydride by the noble metal catalyzed carbonylation of methyl acetate.

The use of catalyst systems comprising noble metals and an iodine compound in the preparation of acetic anhydride by the carbonylation of methyl acetate is well known in the art. Some of this art is disclosed in, for example, Belgian Pat. No. 819,455, British Published patent application No. 2,013,184, Japanese Published patent applications Nos. 75-47921 and 75-47922 and U.S. Pat. Nos. 3,927,078 and 4,046,807. Those publications also disclose that the reaction rate can be increased if the catalyst system contains a promoter such as certain amines, phosphines and inorganic materials such as lithium compounds. The use of amines and phosphines, particularly under reaction conditions giving high space-time yields, causes formation of tars which encapsulate the noble metal catalyst. The use of lithium compounds, such as lithium iodide or lithium acetate, can reduce or retard but not prevent this tar formation. It is also known in the art that the addition of hydrogen in the gas feed to the carbonylation reactor in a system employing triphenylphosphine can also reduce but not eliminate tar formation, see U.S. Pat. No. 4,046,807. Therefore, tar is formed and it is necessary that this tar formed be removed from the reaction system since the tar can reduce catalyst activity and can even result in termination of the carbonylation reaction by the deactivation by encapsulation of the noble metal catalyst.

Moreover, because of the expense of the noble metals, such as rhodium, it is extremely desirable to recover as much of the rhodium as possible from the tar formed in the noble metal catalyzed carbonylation of methyl acetate. A variety of methods have been disclosed in the art for such metal recovery. One such process, for example, is disclosed in U.S. Pat. No. 4,388,217, which discloses an extraction process using methyl iodide and aqueous hydrogen iodide which provides good recovery of the rhodium from the tar formed. This extraction recovers about 90 weight percent of the rhodium from the extracted tar. Attempts have also been made to recover the additional 10 weight percent of rhodium from the tar prior to ashing. One such process is disclosed in U.S. Pat. No. 4,364,907 which discloses further extraction of the aqueous HI extracted tar with aqueous ammonia to remove an additional amount of rhodium from the tar. This process however requires the use of ammonia and subsequent elimination of the ammonia from the process streams which are to be returned to the reaction. It would, therefore, be an advance in the state of the art to provide an improved recovery process for the recovery of increased amounts of noble metals, such as rhodium, from tar formed in carbonylation processes before ashing.

In accordance with the present invention, it has been found that the amount of noble metal, such as rhodium, recovered from the tar can be increased by the addition of a lower fatty acid to the tar and heating the resulting fatty acid tar containing mixture. During heating the noble metal precipitates from the fatty acid tar containing mixture. The precipitated noble metal can then be recovered, for example, by filtration and the fatty acid recovered by distillation from the remaining tar. The remaining tar can then be ashed and any remaining noble metal can be recovered and returned or recycled to the carbonylation process.

Typically, the tar is removed continuously or intermittently from the carbonylation system in the form of a solution in a mixture of the compounds present in the system. The catalyst-tar solution may be removed either from the reactor or, in the case of a system employing a liquid product take-off from the reactor, from some point in the normal catalyst recycle stream. The tar solution can then be concentrated by stripping off some of the liquids present. In production facilities in which the rhodium is recycled to the reactor, the tar containing recycle stream normally will have been concentrated to some extent in the product recovery section of the facilities.

The concentrated noble metal containing tar can if desired be extracted with methyl iodide and aqueous hydrogen iodide and separated into an aqueous phase and an organic tar phase according to U.S. Pat. No. 4,388,217. The aqueous phase contains up to about 90 weight percent of the noble metal present in the tar removed from the reactor. The rhodium in the aqueous phase is recovered and returned to the reactor.

The extracted tar can then be treated with fatty acid containing 1 to 12 carbon atoms such as acetic acid. The mixture is then heated until the noble metal precipitates out of the solution. For example, heating the acetic-acid tar solution at 120° C. for four hours makes the rhodium precipitate out and it can then be recovered by filtration. The rhodium recovered by this acetic acid treatment is about 8 to 9 weight percent of the 10 weight percent of rhodium remaining in the tar after the aqueous iodide extraction. Since acetic acid is used in the reaction as a solvent, the acetic acid in the tar can be recovered by distillation and returned to the reactor. The fatty acid can be any fatty acid containing 2 to about 12 carbon atoms and mixtures of such acids. Such acids are, for example, acetic acid, butyric acid, propanoic acid and the like.

The process in which the tar is formed during the preparation of acetic anhydride by the liquid phase carbonylation of methyl acetate can be a continuous process or a batch process. For example, one such continuous process using rhodium and an iodine compound as catalyst is operated at elevated pressure and temperature wherein a feed mixture containing methyl acetate is continuously fed to a carbonylation reactor and a reaction mixture containing acetic anhydride is continuously removed. Optionally, a catalyst component such as a lithium compound can also be used in such process and up to about 7 volume percent of the carbon monoxide gas may consist of hydrogen to reduce tar formation.

A portion of the reactor liquid contents from such process containing tar, rhodium, iodine, and optionally lithium, catalyst residues is removed from the carbonylation system. The low boiling components such as methyl iodide and methyl acetate along with some acetic acid and acetic anhydride can be removed by heating to provide a concentrated solution of the tar and rhodium catalyst in acetic anhydride and acetic acid. The noble metal catalyst can be recovered from the concentrated solution by the process of this invention without the aqueous iodide extraction. However, preferably the concentrated solution is first extracted by adding methyl iodide and the aqueous hydrogen iodide to the concentrated solution as noted hereinbefore. In some operations, preferred results can be obtained if the methyl iodide is added first to the concentrated solution which has been cooled to just below the boiling point of methyl iodide. After agitation, the aqueous and organic layers are allowed to separate and organic tar containing phase is removed from the bottom of the decanter. The methyl iodide can then be distilled from the organic tar phase to provide an aqueous iodide extracted tar containing solution.

Acetic acid is then added to the aqueous iodide extracted tar containing solution and heated at a temperature of about 120° C. The amount of acetic acid added to the extracted tar can vary depending on, for example, the amount of the tar, the amount of noble metal present in the tar and the efficiency desired of the extraction of the noble metal from the tar. Generally, the amount of acetic acid used is about 1 to 10 parts acetic acid, by weight, to 1 part by weight tar, preferably 1 part to 5 parts acetic acid to 1 part tar.

The heating time can also vary depending on the amount of tar, amount of noble metal present in the tar and efficiency of the extraction desired. For example, about 89 to 98 percent of the noble metal such as rhodium is precipitated out of the tar after heating for a period of 2 to 8 hours, preferably 4 to 6 hours.

The temperature employed is generally the boiling point of the fatty acid. Higher temperatures can be used in pressure equipment. Lower temperatures do not provide the desired treatment of the tar for adequate precipitation of the noble metal from the tar. For example, particularly good recovery results are obtained using acetic acid as the fatty acid in an amount of 1 part extracted tar to 5 parts acetic acid and heated at a temperature of about 120° C. for 3 to 6 hours. The noble metal such as rhodium precipitates out and can be recovered by filtration. The remaining tar can then be ashed to recovery any remaining noble metal present in the tar.

The invention will be further illustrated by the following Examples although it will be understood that these Examples are included merely for purposes of illustration and are not intended to limit the scope of the invention.

EXAMPLE 1

About 1,000 g. of an aqueous iodide extracted tar formed in a carbonylation process using a rhodium catalyst and containing 142 ppm rhodium on assay was concentrated to about 50 g. on a rotary evaporator at about 95° C. for 30 minutes at 5-10 torr. The concentrate was cooled and about 250 ml of acetic acid was added to the extracted tar and the mixture is heated to 120° C. for about six hours. The mixture is then filtered hot to remove the solid rhodium containing precipitate which analyzes as about 11% rhodium. The tar containing mother liquor on assay contained about 12 ppm rhodium. This shows about 98 percent recovery of the rhodium remaining in the extracted tar residue. The acetic acid is recovered from the tar containing mother liquor by distillation. The tar residue may then be ashed and filtered to recover additional rhodium if desired. The rhodium recovered by filtration and ashing can be added back to the reactor.

EXAMPLE 2

About 300 g. of an aqueous iodide extracted tar formed in a carbonylation process using a rhodium catalyst and containing 121 ppm rhodium on assay was concentrated to about 10.5 g. on a rotary evaporator at about 95° C. for 30 minutes at 5-10 torr. The concentrate was cooled and about 50 ml of acetic acid was added to the tar containing residue and the mixture is heated to 120° C. for about six hours. The mixture is then filtered hot to remove the solid rhodium containing precipitate which analyzes as about 13% rhodium. The tar containing mother liquor on assay contained about 13 ppm rhodium. This shows about 98 percent recovery of the rhodium. The acetic acid is recovered from the tar containing mother liquor by distillation. The tar residue may then be ashed and filtered to recover additional rhodium if desired. The rhodium recovered by filtration and ashing can be added back to the reactor.

EXAMPLE 3

About 250 g. of an aqueous iodide extracted tar formed in a carbonylation process using a rhodium catalyst and containing 283 ppm rhodium on assay was concentrated to about 50 g. on a rotary evaporator at about 95° C. for 30 minutes at 5-10 torr. The concentrate was cooled and about 100 ml of acetic acid was added to the tar containing residue and the mixture is heated to 120° C. for about six hours. The mixture is then filtered hot to remove the solid rhodium containing precipitate which analyzes as about 11% rhodium. The tar containing mother liquor on assay contained about 12 ppm rhodium. This shows about 98 percent recovery of the rhodium. The acetic acid is recovered from the tar containing mother liquor by distillation. The tar residue may then be ashed and filtered to recover additional rhodium if desired. The rhodium recovered by filtration and ashing can be added back to the reactor.

EXAMPLE 4

About 1,000 g. of an aqueous iodide extracted tar formed in a carbonylation process using a rhodium catalyst and containing 142 ppm rhodium on assay was concentrated to about 50 g. on a rotary evaporator at about 95° C. for 30 minutes at 5-10 torr. The concentrate was cooled and about 250 ml of butyric acid was added to the tar containing residue and the mixture is heated to 165° C. for about four hours. The mixture is then filtered hot to remove the solid rhodium containing precipitate which analyzes as about 11% rhodium. The tar containing mother liquor on assay contained about 12 ppm rhodium. This shows about 98 percent recovery of the rhodium remaining in the extracted tar residue. The butyric acid is recovered from the tar containing mother liquor by distillation. The tar residue may then be ashed and filtered to recover additional rhodium if desired. The rhodium recovered by filtration and ashing can be added back to the reactor.

Example 4 was repeated except that the mixture was heated to 120° C. rather than 165° C. Essentially the same results were obtained at 120° C. as that obtained at 165° C.

EXAMPLE 5

About 300 g. of an aqueous iodide extracted tar formed in a carbonylation process using a rhodium catalyst and containing 121 ppm rhodium on assay was concentrated to about 10.5 g. on a rotary evaporator at about 95° C. for 30 minutes at 5-10 torr. The concentrate was cooled and about 200 ml of acetic acid was added to the tar containing residue and the mixture is heated to 60° C. for about six hours. The mixture is then filtered hot and no solid rhodium containing precipitate was found. The tar containing mother liquor on assay contained about 121 ppm rhodium. This shows no recovery of the rhodium when the mixture is heated to only about 60° C.

EXAMPLE 6

About 250 g. of an aqueous iodide extracted tar formed in a carbonylation process using a rhodium catalyst and containing 283 ppm rhodium on assay was concentrated to about 50 g. on a rotary evaporator at about 95° C. for 30 minutes at 5-10 torr. The concentrate was cooled and about 100 ml of acetic acid was added to the tar containing residue and the mixture is heated at 100° C. for about six hours. The mixture is then filtered hot to remove the solid rhodium containing precipitate which analyzes as about 11% rhodium. The tar containing mother liquor on assay contained about 12 ppm rhodium. This shows about 98 percent recovery of the rhodium. The acetic acid is recovered from the tar containing mother liquor by distillation. The tar residue may then be ashed and filtered to recover additional rhodium if desired. The rhodium recovered by filtration and ashing can be added back to the reactor.

The invention has been described in detail with particular reference to preferred embodiments thereof, but it will be understood that variations and modifications can be effected within the spirit and scope of the invention.

I claim:

1. Process for the recovery of noble metal from a noble metal containing tar formed in a process in which acetic anhydride is prepared by carbonylating methyl acetate in the presence of a noble metal catalyst, wherein said noble metal containing tar is mixed with about 1 part by weight tar to 1 to 10 parts of a lower fatty acid having 2 to 12 carbon atoms and heated at a temperature of at least 100° C. to precipitate said noble metal catalyst from said tar.

2. A process according to claim 1 wherein said fatty acid is acetic acid.

3. A process according to claim 1 wherein said noble metal is rhodium.

4. Process for the recovery of rhodium from a rhodium containing tar formed in a process derived from a production in which acetic anhydride is prepared by carbonylating methyl acetate in the presence of a rhodium catalyst, wherein said rhodium containing tar solution is mixed with about 1 part by weight tar to 1 to 10 parts by weight acetic acid and heated at a temperature of at least 100° C. for a period of 4 to 6 hours and recovering rhodium from said tar containing acetic acid mixture.

* * * * *